United States Patent
Haack et al.

(10) Patent No.: US 9,981,875 B2
(45) Date of Patent: May 29, 2018

(54) ALKALINE-TREATED INVERTED MOLASSES AS DISPERSANTS FOR MINERAL SUSPENSIONS

(71) Applicant: SIKA TECHNOLOGY AG, Baar (CH)

(72) Inventors: Thomas Haack, Santiago de Chile (CL); Hugo Olivares, Santiago Centro (CL); Pedro Gallegos, Santiago de Chile (CL)

(*) Notice: Subject to any disclaimer, the term of this patent is extended or adjusted under 35 U.S.C. 154(b) by 0 days. days.

(21) Appl. No.: 15/028,604

(22) PCT Filed: Oct. 15, 2014

(86) PCT No.: PCT/EP2014/072133
§ 371 (c)(1),
(2) Date: Jul. 25, 2016

(87) PCT Pub. No.: WO2015/055725
PCT Pub. Date: Apr. 23, 2015

(65) Prior Publication Data
US 2016/0347660 A1   Dec. 1, 2016

(30) Foreign Application Priority Data
Oct. 18, 2013 (EP) .................................... 13004985

(51) Int. Cl.
C04B 24/10 (2006.01)
C04B 40/00 (2006.01)
C04B 24/26 (2006.01)
C08K 5/1535 (2006.01)
C04B 103/40 (2006.01)

(52) U.S. Cl.
CPC .......... C04B 24/10 (2013.01); C04B 24/2641 (2013.01); C04B 40/0039 (2013.01); C08K 5/1535 (2013.01); C12Y 302/01026 (2013.01); C04B 2103/408 (2013.01)

(58) Field of Classification Search
CPC .................................................. C04B 24/10
See application file for complete search history.

(56) References Cited

U.S. PATENT DOCUMENTS

| | | | |
|---|---|---|---|
| 3,536,507 A | 10/1970 | Klein et al. | |
| 3,594,203 A * | 7/1971 | Sawyer | C04B 33/13 106/484 |
| 5,106,517 A * | 4/1992 | Sheu | C09K 8/08 507/110 |
| 5,110,484 A * | 5/1992 | Sheu | C09K 8/08 507/110 |
| 6,897,047 B1 * | 5/2005 | Takasaki | C12N 9/90 435/105 |
| 2008/0011201 A1 * | 1/2008 | Strachan | B01F 17/0085 106/795 |
| 2011/0160349 A1 | 6/2011 | Frunz et al. | |
| 2012/0135479 A1 * | 5/2012 | Dillon | C10L 1/026 435/134 |
| 2013/0344543 A1 * | 12/2013 | Kurihara | C13K 1/02 435/99 |
| 2014/0135427 A1 * | 5/2014 | Gallegos | C04B 40/0042 524/3 |

FOREIGN PATENT DOCUMENTS

| | | | |
|---|---|---|---|
| EP | 2159203 A1 | 3/2010 | |
| EP | 2559675 A1 | 2/2013 | |
| WO | 02/083592 A1 | 10/2002 | |
| WO | 2005/110941 A1 | 11/2005 | |
| WO | WO 2012155342 A1 * | 11/2012 | ............. C04B 24/38 |

OTHER PUBLICATIONS

Zhang et al. (Journal of Wuhan University of Technology—Mater. Sci. Ed, 2007, 245-249).*
Kronlof (Materials and Structures, 1994, 27, 15-25).*
Feb. 17, 2015 Search Report issued in International Patent Application No. PCT/EP2014/072133.

* cited by examiner

Primary Examiner — Liam J Heincer
(74) Attorney, Agent, or Firm — Oliff PLC

(57) ABSTRACT

Modified molasses are used as dispersants for mineral suspensions, the modified molasses being obtained by means of a method comprising the steps: a) inversion of molasses and/or provision of inverted molasses; b) reaction of the inverted molasses with alkalis.

24 Claims, No Drawings

ALKALINE-TREATED INVERTED MOLASSES AS DISPERSANTS FOR MINERAL SUSPENSIONS

TECHNICAL FIELD

The invention relates to the use of modified molasses as dispersants for mineral suspensions. The invention relates further to a method for producing a mineral suspension, to a corresponding mineral suspension, and to molded bodies obtainable therefrom.

PRIOR ART

Suspensions are heterogeneous mixtures of substances which comprise a liquid with solid particles dispersed therein. In order to stabilize suspensions or purposively influence their properties, so-called dispersants are conventionally used.

An example of suspensions are workable mineral binder compositions, for example mortar or concrete compositions, tempered with water. Such compositions are conventionally treated with dispersants in order to improve their workability or reduce the amount of water needed. Known dispersants for mineral binder compositions are inter alia polycarboxylate ethers, lignosulfonates, naphthalene sulfonate-formaldehyde condensates, saccharides and the like.

Other examples of suspensions are so-called tailings or dressing residues. These are fine-grained rock residues in the form of slurry which are left behind in ore mining after the valuable ore has been separated from the rock. Tailings are conveyed from the mines or ore processing sites to large storage facilities (for example artificially produced basins), where they are stored. The tailings are thereby concentrated in concentrators to a solids content of 45% and then transported to the storage facilities by means of powerful pumps. It is important on the one hand that the tailings have good flow behavior so that they can be pumped as a non-Newtonian fluid. On the other hand, the tailings should, where possible, not be too liquid so that they do not flow over the dam. In addition, it would be very advantageous to be able to concentrate the tailings further in order to save further water, which is particularly relevant in regions in which there is a water shortage or water is very expensive. However, this is scarcely possible at present owing to the exponentially increasing viscosity of the tailings.

WO 02/083592 A1 (Betzdearborn Inc.) describes in this context various polymers, for example polymethacrylates, as viscosity modifiers for tailings. However, with regard to the problems mentioned above, these are not wholly satisfactory.

Moreover, many of the dispersants used today are based on raw materials which are obtained from mineral oil. For ecological and economic reasons, dispersants based on renewable raw materials or by-products of industrial processes are becoming increasingly important.

WO 2005/110941 A1 (Australian Industrial Additives) discloses, for example, the use of chemically degraded molasses as a dispersant or as a grinding aid.

However, there is a continued need for new or alternative dispersants which, where possible, produce a good dispersing action in mineral suspensions of different compositions or independently of the respective intended use.

DESCRIPTION OF THE INVENTION

Accordingly, the object of the present invention is to provide a dispersant for use in mineral suspensions.

The dispersant is to be effective in particular independently of the composition of the mineral suspension, and is to be as inexpensive as possible to produce. In particular, the dispersant is to develop a good dispersing or liquefying action, which is maintained over a prolonged period, in mineral binder compositions, for example in hydraulic-setting binders, in particular without retarding the hardening of the binder composition too greatly. The dispersant is likewise to be suitable for liquefying fine-grained suspensions, for example in the form of tailings, having as high a solids content as possible.

Surprisingly, it has been found that this can be achieved by the use of modified molasses as dispersants according to independent main claim 1. The core of the invention is accordingly the use of modified molasses, or alkaline-treated inverted molasses.

Molasses is a waste product or by-product of the production of sugar from sugar cane, sugar beet or sweet sorghum. The molasses modified according to the present invention leads to significantly improved dispersing properties in very different mineral suspensions, such as, for example, in mineral binder compositions or in tailings.

When the modified molasses is used as a dispersant in mineral binder compositions, in particular in cement compositions, it is possible, without further admixtures, to produce binder compositions which have virtually constant workability over a prolonged period but nevertheless harden relatively quickly.

The dispersant according to the invention additionally makes use of readily available and inexpensive starting materials which are formed inter alia as by-products or waste products in sugar production. This is correspondingly resource-saving.

Further aspects of the present invention are a method for producing a mineral suspension, and corresponding suspensions which comprise the dispersant used according to the invention.

Further advantageous embodiments of the invention will become apparent from the dependent claims.

WAYS OF CARRYING OUT THE INVENTION

According to a first aspect, the present invention relates to the use of modified molasses as dispersants for mineral suspensions, wherein the modified molasses is obtainable by a method comprising the steps:
a) inverting molasses and/or providing inverted molasses,
b) reacting the inverted molasses with alkalis.

Step b) is in particular carried out after step a).

In the present context, the expression "mineral suspension" denotes a suspension comprising a liquid, in particular water, as well as a plurality of mineral particles at least partially suspended therein. The suspension can also be referred to as a slurry. The expression explicitly also includes mineral binder compositions, for example mortar or concrete compositions, which have been tempered with water and are in particular in the flowable or pasty state. The mineral suspension has in particular a solids content of at least 25% by weight, in particular at least 30% by weight, preferably from 50 to 95% by weight, advantageously from 60 to 90% by weight, especially from 70 to 85% by weight, based on the total weight of the suspension.

Molasses is formed as a by-product in the production of sugar from sugar cane, sugar beet and sweet sorghum. Molasses typically contains from 30 to 65% by weight sucrose, depending on its origin. Sucrose thereby forms in particular the main constituent of the molasses or the constituent with the greatest proportion by weight. Organic acids, vitamins and/or minerals are also present in the molasses. As a by-product or waste product, molasses is available in large amounts and is an inexpensive source for the production of dispersants for mineral suspensions.

Molasses from sugar cane, sugar beet and/or sweet sorghum has been found to be particularly advantageous. Sugar-cane molasses is preferably used in the present invention. However, any other molasses can in principle also be used.

"Inverting of molasses" is to be understood as meaning the enzymatic or acid-catalyzed cleavage or hydrolysis of the saccharides present in the molasses to form the monosaccharides fruit sugar (fructose) and grape sugar (glucose). The inverted molasses contains the monosaccharides fructose and glucose, in particular in the molar ratio fructose:glucose of from 40:60 to 60:40 or from 45:55 to 55:45, especially in equal molar proportions.

The preferred inverting in the present invention is enzymatic inverting. In this case, the inverted molasses contains, in addition to the monosaccharides, in particular also the enzyme used and/or fragments thereof.

The enzyme used in the enzymatic inverting is in particular an invertase. In other words, the enzymatically inverted molasses is in particular molasses inverted by invertase. Invertase is classified under EC number (Enzyme Commission number) 3.2.1.26 and belongs to the category of the glycosidases. Other names for invertase are 3-fructofuranosidase, saccharase or invertin.

Suitable temperatures for the enzymatic inverting of molasses are in particular in the range of from 20 to 80° C., preferably from 30 to 70° C., in particular from 55 to 65° C. Furthermore, the molasses to be inverted is advantageously inverted at a pH of from 4 to 7, in particular from 4.5 to 6.5. Under such conditions, an optimal conversion of molasses is achieved with a minimal amount of enzyme, which is advantageous for economic reasons.

Other conditions are, however, also possible in principle. However, at temperatures above 80° C. and/or pH values <3 or >9, there is the risk of at least partial denaturing of the enzymes, which under certain circumstances increases the proportion of undesirable secondary products in the inverted molasses.

Accordingly, the enzymatically inverted molasses used is preferably molasses inverted at a temperature of from 20 to 80° C., in particular from 30 to 70° C., especially from 55 to 65° C., and/or at a pH of from 4 to 7, in particular from 4.5 to 6.5.

The enzyme used, or the invertase, has, for example, an activity in the range of from 100,000 to 300,000 S.U., preferably from 180,000 to 220,000 S.U., especially 200,000 S.U. 1 S.U. (Sumner unit) is defined as the amount of enzyme that releases 1 mg of inverted sucrose from 6 ml of a 5.4% strength sucrose solution within a period of 5 minutes at a temperature of 20° C. and a pH of 4.7.

The concentration of invertase, in particular having an activity of from 100,000 to 300,000 S.U., is advantageously from 30 to 80 ppm, preferably from 40 to 60 ppm, parts by weight of invertase per part by weight of sucrose to be inverted that is present in the molasses. In the case of invertases having lower activities, the concentration can be correspondingly increased, and in the case of invertases having higher activities, the concentration can be correspondingly reduced.

The molasses to be inverted is incubated with the invertase in particular for from 0.5 to 15 hours, preferably from 1 to 12 hours, in step a).

The inverting according to the invention of the molasses can in principle also take place by acid-catalyzed hydrolysis. For the acid-catalyzed hydrolysis, the solution is lowered to a suitable pH by addition of an acid. To that end, the pH of the molasses, which is typically approximately pH 7, is lowered to a pH of from 1 to 4, preferably from 2 to 3, by stirring in, for example, sulfuric acid (from 0.5 to 5% by weight, preferably from 1 to 3% by weight, most preferably 2% by weight in $H_2O$). The acidified molasses is then incubated for a period of from 2 to 8 hours, preferably from 3 to 6 hours, most preferably for 4.5 hours.

Enzymatically inverted molasses and molasses catalyzed by acid are chemically different. As compared with enzymatically inverted molasses, molasses catalyzed by acid contains in particular a large number of additional secondary products, which are formed inter alia by the reaction of the acid with the further constituents of the molasses (for example organic acids, vitamins, etc.). Such secondary products are found in enzymatically inverted molasses either in only a small amount or not at all, owing to the high selectivity of the enzymes. In some applications, the secondary products can have an adverse effect under certain circumstances.

Before the inverting or before step a), the molasses is diluted preferably with from 0.2 to 0.8, especially with from 0.5 to 0.7, part by weight of water per part by weight of molasses. More effective inverting is achieved as a result.

The inverting in step a) is in particular continued until a degree of conversion of at least 50%, in particular at least 60%, preferably at least 75%, more preferably at least 90%, yet more preferably at least 95%, is reached. The degree of conversion indicates the ratio of the amount of inverted sucrose to the amount of sucrose originally present in the molasses.

The progress of the inverting reaction or the conversion of the sucrose can be monitored, for example, by Fourier transform infrared spectroscopy on the basis of the sucrose band at 984 $cm^{-1}$. The degree of conversion can be determined directly therefrom. This technique is known per se to the person skilled in the art.

A ratio by weight of inverted sucrose to non-inverted sucrose in the inverted molasses is advantageously at least 1, in particular at least 3, especially at least 5, particularly preferably at least 10 or 20. This is the case in particular independently of the type of inverting.

The inverted molasses used in step b) advantageously has a solids content of from 30 to 70 percent by weight, preferably from 40 to 60 percent by weight. The solids content can be adjusted in a manner known per se by dilution (for example by adding water) or concentration (for example by evaporating off excess water).

During step b), the inverted molasses is reacted with alkalis. In the present context, the term "alkalis" denotes in particular substances which form alkaline solutions with water or substances which, when added to an aqueous solution, are capable of raising the pH of the solution. In alkaline solutions, the concentration of $OH^-$ ions exceeds that of $H_3O^+$ ions, or the pH of the alkaline solution is greater than 7.

The reaction of the inverted molasses in step b) takes place in such a manner that at least some of the monosaccharides present in the inverted molasses are oxidized. The reaction in step b) is thus different from a simple pH change by means of alkalis.

In the reaction, in particular aldehyde groups and/or primary terminal HO groups of the reducing monosaccharides (for example glucose and fructose) present in the inverted molasses are oxidized to acid groups and rearranged in subsequent reactions, whereby oxidized fragments form. Accordingly, the alkaline-reacted inverted molasses comprises in particular sugar acids or C1 to C6 polyhydroxycarboxylic acids, for example gluconic acid and citric acid. Furthermore, it is to be assumed that further constituents of the inverted molasses are also modified chemically by the alkaline treatment. Accordingly, alkaline-reacted inverted molasses is a complex mixture of different substances.

The reaction in step b) is in particular continued until a degree of conversion of at least 50%, in particular at least 60%, preferably at least 75%, more preferably at least 90%, yet more preferably at least 95%, is achieved. The degree of conversion indicates the weight ratio of the amount of oxidized monosaccharides or polyhydroxycarboxylic acids to the amount of monosaccharides originally present in the inverted molasses.

The reaction can again be monitored, for example, by Fourier transform infrared spectroscopy.

A ratio by weight of oxidized monosaccharides or polyhydroxycarboxylic acids to non-oxidized monosaccharides in the alkaline-reacted inverted molasses is advantageously at least 1, in particular at least 3, especially at least 5, particularly preferably at least 10 or 20.

Step b) is carried out in particular at a pH of from 6 to 14, preferably from 6 to 12 and most preferably from 8 to 12 or from 9 to 12. That pH is kept constant in particular for from 0.5 to 5 hours, preferably for from 1.5 to 4 hours, most preferably for from 2 to 3 hours.

In particular, the alkaline reaction in step b) is carried out by adding a base. A base is preferably from the group consisting of $Ca(OH)_2$, $Mg(OH)_2$, NaOH, KOH or mixtures thereof. KOH and NaOH are particularly preferred bases. NaOH is most preferred.

The base employed in step b) is advantageously used in the form of an aqueous solution of the base. The preferred concentration of the base in the aqueous solution is from 10 to 70% by weight, in particular from 15 to 30% by weight, for example 23% by weight. As a result, the base can easily be metered in and the reaction in step b), in particular the temperature and/or the pH, is easier to control.

Preferably, step b) is carried out at a temperature of from 10° C. to 90° C., preferably from 30° C. to 80° C., most preferably from 35° C. to 75° C. or from 50 to 70° C. That temperature is kept constant in particular for from 0.5 to 5 hours, preferably for from 1.5 to 4 hours, most preferably for from 2 to 3 hours.

Most particularly preferably, a temperature of from 30° C. to 80° C., preferably from 40° C. to 70° C. and most preferably from 55 to 65° C., and/or a pH of from 6 to 14, preferably from 6 to 12, in particular from 9 to 12 and most preferably from 7 to 11 or from 8 to 10, is maintained in step b) for from 0.5 to 5 hours, preferably for from 1.5 to 4 hours, most preferably for from 2 to 3 hours.

The temperature and/or the pH during the reaction in step b) can be controlled in particular by the rate of addition of the base. On account of the alkaline reaction of the inverted molasses or the addition of the base in step b), the temperature and/or the pH of the reaction solution typically increases.

Accordingly, the base is advantageously so metered in in step b) that the above-mentioned temperatures and/or pH values are maintained. If helpful, the reaction solution can additionally be cooled or heated during step b).

According to a preferred embodiment, the modified molasses is used together with at least one liquefier.

The at least one liquefier is in particular selected from the group consisting of lignosulfonates, sulfonated naphthalene-formaldehyde condensates, sulfonated melamine-formaldehyde condensates, polycarboxylates and/or polycarboxylate ethers (PCE).

In particular, the liquefier has a structure according to formula (I)

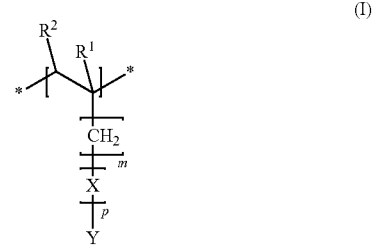

wherein
$R^1$, independently of one another, represents H or an alkyl group having from 1 to 5 carbon atoms,
$R^2$, independently of one another, represents H, —COOM, or an alkyl group having from 1 to 5 carbon atoms,
M, independently of one another, represents an alkali metal ion, an alkaline earth metal ion, a di- or tri-valent metal ion, an ammonium ion, or an organic ammonium group,
X represents —COO—, —NH— or mixtures thereof,
m=0, 1 or 2,
p=0 or 1,
Y, independently of one another, represents H, M, a $C_1$- to $C_{20}$-alkyl group, -cycloalkyl group, -alkylaryl group, -hydroxyalkyl group, or a group of the formula -[AO]$_n$—$R^a$, wherein the mentioned groups are unsubstituted or substituted by a sulfone group, a sulfate group or by a phosphate group,
wherein A=$C_2$- to $C_4$-alkylene, $R^a$ represents H, a $C_1$- to $C_{20}$-alkyl group, -cyclohexyl group or -alkylaryl group, and n=1-10.

Some of the compounds of formula I are available commercially, or they can be prepared in a manner known per se, for example by radical polymerization of unsaturated monomers of formula II

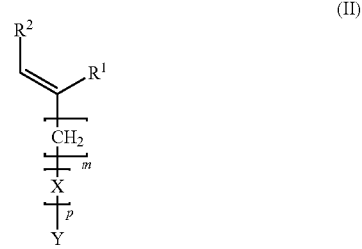

$R^1$, $R^2$, X, Y, m and p in formula II are defined as described above in connection with the structure according to formula I.

Preference is given to a liquefier according to formula I wherein $R^1$ represents H or a methyl group. $R^2$ is advantageously H.

According to a preferred embodiment, X represents —COO—. Advantageously, m=0 and/or p=1. Y is in particular M or H.

The at least one liquefier includes in particular a poly(meth)acrylic acid and/or a salt thereof. The expression "poly(meth)acrylic acid" denotes a polymer or a copolymer consisting substantially of acrylic acid monomers, methacrylic acid monomers, mixtures of acrylic acid monomers and methacrylic acid monomers and/or salts of those monomers. The proportion of the mentioned monomers is in particular >90 mol %, preferably >96 mol %, especially >99 mol %, based on all the monomers present in the poly(meth)acrylic acid.

Advantageously, the at least one liquefier includes a polyacrylic acid and/or a salt thereof.

The molecular weight of the at least one liquefier is advantageously in the range of from 1000 to 10,000 g/mol, in particular from 2000 to 8000 g/mol, preferably from 3000 to 7000, more preferably from 3500 to 6500 g/mol. This is the case in particular if the liquefier has a structure according to formula I or is a poly(meth)acrylic acid and/or a salt thereof, in particular a polyacrylic acid and/or a salt thereof. The molecular weight can be determined in a manner known per se by gel permeation chromatography (GPC) with aqueous eluants. For the calibration there is preferably used a narrowly calibrated polyethylene glycol standard.

Preferably, the ratio by weight of the at least one liquefier and the modified molasses is in the range of from 5:95 to 95:5, in particular from 10:90 to 90:10, preferably from 30:70 to 70:30, especially from 40:60 to 60:40 or from 45:55 to 55:45.

If the mineral suspension is, for example, a fine-grained suspension or tailings, as are described hereinbelow, the use of combinations of modified molasses and liquefiers having a structure according to formula I or liquefiers including poly(meth)acrylic acids and/or salts thereof, in particular polyacrylic acid and/or salts thereof, has been found to be particularly suitable. Particularly advantageously, liquefiers having the above-mentioned molecular weights are used, and the mentioned ratios by weight are observed. It has been found that such combinations can cause synergistic effects, as a result of which particularly effective dispersion or viscosity reduction can be achieved.

In connection with mineral suspensions which comprise mineral binders, in particular mortar or cement compositions, the use of combinations of modified molasses and liquefiers selected from the group consisting of lignosulfonates, sulfonated naphthalene-formaldehyde condensates, sulfonated melamine-formaldehyde condensates, and/or polycarboxylate ethers has been found to be especially suitable. Lignosulfonates are particularly advantageous as liquefiers.

By combining conventional liquefiers with modified molasses, the amount of conventional liquefiers, for example, can be reduced significantly. This is of interest in particular in the case where there is a shortage of conventional liquefiers or the price thereof is increasing.

The mineral suspension generally has, for example, a solids content of from 20 to 95% by weight, especially from 50 to 90% by weight, in particular from 55 to 85% by weight, preferably from 60 to 75% by weight.

The pH of the mineral suspension can be in a range of, for example, from 4 to 14, in particular from 4 to 11, preferably from 5 to 10, in particular from 6 to 9.

The modified molasses, optionally together with the at least one liquefier, is typically used in an amount of from 0.01 to 5% by weight, preferably from 0.1 to 1% by weight, especially from 0.4 to 0.8% by weight, based on the solids content of the suspension. The amounts are based in particular on the total amount of modified molasses plus liquefier.

According to a first particularly advantageous embodiment, the mineral suspension is a fine-grained suspension.

The amount by weight of solid particles having a particle size <100 μm in the mineral suspension is in particular at least 50% by weight, preferably at least 75% by weight, in particular at least 90% by weight or at least 95% by weight, based on the total weight of all the solids in the mineral suspension.

In particular, the amount by weight of solid particles having a particle size >10 mm in the mineral suspension is less than 10% by weight, preferably less than 5% by weight. In particular less than 1% by weight, based on the total weight of all the solids in the mineral suspension.

The amount by weight of solid particles having a particle size >1 mm is advantageously less than 10% by weight, preferably less than 5% by weight. In particular less than 1% by weight, based on the total weight of all the solids in the mineral suspension.

The amount by weight of solid particles having a particle size <100 μm in the mineral suspension is in particular at least 50%, preferably at least 75%, in particular at least 90% or at least 95%, based on the total weight of all the solids in the mineral suspension.

In the case of a fine-grained suspension, the modified molasses, optionally together with the at least one liquefier, is used preferably in an amount of from 0.01 to 1% by weight, especially from 0.01 to 0.8% by weight or from 0.01 to 0.6% by weight, based on the total weight of the mineral suspension. The amounts are based in particular on the total amount of modified molasses plus liquefier.

The particle size can be determined in particular by sieve analysis, for example using a sieve having square openings, in a manner known per se.

In particular, the mineral suspension is substantially free of cement or of hydraulic binders or of mineral binders. This means that the amount of such substances in the mineral suspension is less than 5% by weight, preferably less than 2% by weight, in particular less than 1% by weight or less than 0.1% by weight.

The mineral suspension, in particular the fine-grained suspension, can comprise or consist of tailings, for example. In the present case, the term "tailings" is to be understood as meaning fine-grained residues from ore dressing, which are in particular in the form of aqueous slurries.

The tailings consist substantially of fine-grained mineral substances and water. The mineral substances include in particular metals, metal oxides, silicon dioxide, sulfur, phosphorus.

The tailings are preferably substantially free of cement or of hydraulic binders or of mineral binders, as is defined above.

The pH of the tailings is preferably in a range of from 4 to 11, preferably from 5 to 10, in particular from 6 to 9.

According to another preferred embodiment, the mineral suspension comprises a mineral binder. In this case, the mineral suspension can preferably also contain coarse-grained solid particles.

The expression "mineral binder" is to be understood as meaning in particular a binder which reacts in the presence of water in a hydration reaction to form solid hydrates or hydrate phases. It can be, for example, a hydraulic binder (for example cement or hydraulic lime), a latent hydraulic binder (for example slag), a pozzolanic binder (for example fly ash) or a non-hydraulic binder (gypsum or white lime).

A "cementitious binder" is understood in the present case as being in particular a binder or a binder composition having a content of cement clinker of at least 5% by weight, in particular at least 20% by weight, preferably at least 35% by weight, especially at least 65% by weight. The cement clinker is preferably a Portland cement clinker. In the present context, cement clinker means in particular ground cement clinker.

A "mineral binder composition" accordingly denotes a composition comprising a mineral binder and, where appropriate, further components, such as, for example, aggregates, water and/or admixtures.

In particular, the mineral binder or the mineral binder composition comprises a hydraulic binder, preferably cement. Particular preference is given to a cement having a cement clinker content of ≥35% by weight. The cement is in particular of type CEM I, CEM II and/or CEM IIIA (according to standard EN 197-1). The amount of hydraulic binder in the mineral binder as a whole is advantageously at least 5% by weight, in particular at least 20% by weight, preferably at least 35% by weight, especially at least 65% by weight. According to a further advantageous embodiment, the mineral binder consists of ≥95% by weight hydraulic binder, in particular cement clinker.

It can, however, also be advantageous if the binder or the binder composition comprises or consists of other binders. Other binders are in particular latent hydraulic binders and/or pozzolanic binders. Suitable latent hydraulic and/or pozzolanic binders are, for example, slag, fly ash and/or silica fume. The binder composition can likewise comprise inert substances such as, for example, limestone, quartz powders and/or pigments. In an advantageous embodiment, the mineral binder comprises from 5 to 95% by weight, in particular from 5 to 65% by weight, particularly preferably from 15 to 35% by weight, latent hydraulic and/or pozzolanic binders. Advantageous latent hydraulic and/or pozzolanic binders are slag and/or fly ash.

In a particularly preferred embodiment, the mineral binder comprises a hydraulic binder, in particular cement or cement clinker, and a latent hydraulic and/or pozzolanic binder, preferably slag and/or fly ash. The amount of latent hydraulic and/or pozzolanic binder is particularly preferably from 5 to 65% by weight, particularly preferably from 15 to 35% by weight, while at least 35% by weight, especially at least 65% by weight, of the hydraulic binder are present.

In addition to the mineral binder, the mineral suspension can comprise, for example, solid aggregates, such as gravel, sand and/or rock fragments. The mineral suspension is accordingly in particular a mortar composition or a concrete composition.

The modified molasses can also be used together with further substances, in particular with cement additives or concrete admixtures, such as, for example, grinding aids, antifoams, colorants, preservatives, air-entraining agents, shrinkage reducing admixtures, further liquefiers and/or corrosion inhibitors.

In the case of a suspension comprising a mineral binder, the modified molasses is used in the mineral suspension preferably in an amount of from 0.1 to 1% by weight, especially from 0.4 to 0.8% by weight, based on the weight of the mineral binder.

In particular, the ratio by weight of water to mineral binder in the mineral suspension is from 0.25 to 0.8, in particular from 0.3 to 0.7, preferably from 0.4 to 0.6.

By using the modified molasses in mineral binders or mineral binder compositions, a very good liquefying action is achieved, which is maintained even over a prolonged period. The setting of the binder is not retarded substantially.

The modified molasses can accordingly be used as a dispersant or liquefier for a mineral binder or a mineral binder composition.

As has been found, the use of the modified molasses allows the flow limit and/or viscosity of the mineral suspension to be lowered considerably even when the suspension has a low liquid content or a high solids content. This is the case in particular in fine-grained suspensions and at low doses.

Accordingly, the modified molasses, in particular together with at least one further liquefier, can be used for purposively lowering the flow limit and/or viscosity of mineral suspensions, in particular of fine-grained suspensions or tailings.

A further aspect of the present invention relates to a method for producing a mineral suspension, wherein modified molasses as described above, optionally together with at least one liquefier, is mixed with mineral solid particles and a liquid, in particular water.

The modified molasses, the at least one liquefier and the mineral suspension are in particular as defined above.

The mineral solid particles and the liquid can be present, for example, in premixed form as a suspension and can be mixed in that form with the modified molasses and optionally with the at least one liquefier. For example, the modified molasses, optionally together with the at least one liquefier, can be mixed with a mineral suspension in the form of tailings.

It is, however, also possible to premix the modified molasses, in particular together with the at least one liquefier, with at least a portion of the mineral solid particles, in particular in dry form, and then to mix the premixture with the water and, where appropriate, further components.

In an analogous manner, the modified molasses, and in particular the at least one liquefier, can be premixed with at least a portion of the water and then mixed with the solid particles and, where appropriate, further water. For example, the modified molasses, and in particular the at least one liquefier, can be added to the tempering water when tempering a mineral binder composition, and the tempering water is then added to the mineral binder and, where appropriate, further components.

The present invention further includes a suspension obtainable by the method described above.

The present invention will be explained in the following by means of implementation examples. Further advantageous embodiments of the present invention will become apparent from the implementation examples and the totality of the patent claims.

Implementation Examples

1. Production of Modified Molasses 1.1 Inverting of Molasses

In order to produce enzymatically inverted sucrose, untreated molasses from the production of sugar from cane sugar is converted into inverted molasses. Untreated molasses from cane sugar has a sucrose content of from 30 to 40% by weight.

Untreated molasses (solids content approximately 80% by weight; pH=5.5) is diluted with water (0.60 part by weight of water per part by weight of molasses) in a heatable reactor, with stirring. The reactor is then adjusted to a predetermined temperature of 60° C., and 50 ppm (parts by weight, based on sucrose) of invertase (activity: 200,000

S.U.; obtainable, for example, from BioCat GmbH, Germany; dissolved in 500 ppm of water) are added. The reaction mixture so obtained is then kept at the predetermined temperature for 8 hours, whereby at least 95% of the sucrose originally present in the molasses are converted into inverted sucrose. The progress of the reaction can be monitored by Fourier transform infrared spectroscopy on the basis of the sucrose band at 984 cm$^{-1}$. There is obtained a liquid of substantially homogeneous consistency with a solids content of 49% by weight and a pH of 5.3, which is referred to in the following as inverted molasses IM.

1.2 Reaction of the Inverted Molasses with Alkalis

Sodium hydroxide solution (50% by weight NaOH in water) is then added in portions to the molasses so inverted IM over a period of approximately 1 hour. As a result of the addition of the sodium hydroxide solution, the pH and temperature increase (as a result of exothermic reactions). The addition was carried out in such a manner that the pH of the reaction solution is in the range of from 6.9 to 12.3 throughout and the temperature of the reaction solution is in the range of from 20 to 77° C. The pH is kept constant in a range of from 9.7 to 10.4 over a period of 2.5 hours by the rate of addition of the sodium hydroxide solution. The temperature was likewise kept constant in a range of from 59 to 64° C. for 2.5 hours. A degree of conversion of at least 95% is thereby achieved. In other words, at least 95% of the monosaccharides originally present in the inverted molasses are reacted. The progress of the reaction is monitored by Fourier transform infrared spectroscopy on the basis of the carboxylate band at 1580 cm$^{-1}$.

There is obtained a liquid of substantially homogeneous consistency, which is referred to in the following as modified molasses or alkaline-reacted inverted molasses DM.

2. Production of Modified Glucose (Comparative Test)

For the production of comparative samples, glucose was subjected to an alkaline treatment. Specifically, dilute sodium hydroxide solution (23% by weight NaOH in water) was added in portions to an aqueous glucose solution (50% by weight glucose in water). The procedure was substantially as described in section 1.2.

There was obtained a solution comprising approximately 38.5% by weight carboxylic acids or phenols and <0.4% glucose, which is referred to in the following as modified glucose DG. The modified glucose DG had a solids content of approximately 64.8% by weight and a pH of 8.9.

3. Function Tests in Mineral Binders

The activity of the molasses modified according to the invention was tested in cement pastes.

The cement paste was prepared by homogeneously mixing 100 g of cement (Bio Bio AR; type CEM I; obtainable from Cementos Bio Bio S.A, Chile), 0.6 g of the respective dispersant indicated in Table 1 (DM, IM, DG or Vixil) and 55 g of water for 4 minutes by means of a mechanical mixer. In order to ensure comparability, all the dispersants were diluted to a solids content of 40% by weight.

In order to determine the activity of the dispersants, the slump of the cement pastes was measured immediately after tempering (=slump after 0 minutes) and after 30 minutes and after 60 minutes in accordance with BS EN 12350-2. The change in temperature of the cement pastes was likewise recorded in order to monitor the hydration or setting behavior of the cement pastes after tempering, and the time ($t_{max}$) to the occurrence of the overall temperature maximum was determined.

Table 1 gives an overview of the tests carried out and the results thereof.

TABLE 1

| Dispersant | $t_{max}$ [h:mm] | Slump [mm] | | |
|---|---|---|---|---|
| | | after 0 min. | after 30 min. | after 60 min. |
| DM$^{(modified\ molasses)}$ | 9:37 | 177 | 139 | 139 |
| IM$^{(inverted\ molasses)}$ | 12:40 | 170 | 130 | 120 |
| DG$^{(modified\ glucose)}$ | 12:01 | 175 | 138 | 127 |
| Vixil* | 10:07 | 179 | 133 | 147 |

*= sodium lignosulfonate (obtainable from Booregaard)

It is apparent from Table 1 that modified molasses DM has a liquefying action has a liquefying action comparable to that of lignosulfonate (Vixil) but at the same time clearly has a less pronounced retarding effect than does lignosulfonate.

Both inverted molasses (IM) and modified glucose DG cause in particular a significantly greater retardation than modified molasses DM.

The molasses modified according to the invention is therefore a suitable and advantageous dispersant for mineral binder compositions.

4. Function Tests with Tailings

The activity of the molasses modified according to the invention was further tested in tailings.

4.1 Tailings

Tailings used:

MEL tailings: Mineria Escondida Ltd. (Chile); 63.5% by weight solids content; >99% by weight of the particles have a particle size <100 μm (based on the total weight of all the solids present in the tailings).

DSAL tailings: Codelco, División Salvador; pH 8.4; 66.83% by weight solids content; >99% by weight of the particles have a particle size <100 μm (based on the total weight of all the particles present in the tailings).

4.3 Dispersants

In addition to the modified molasses DM and the inverted molasses IM, the following dispersants were used:

| Abbreviation | Substance |
|---|---|
| M | untreated molasses as described in section 1.1 |
| PAA | polyacrylic acid having a molecular weight of 4500 g/mol |
| PCE | polycarboxylate ether; Sika ViscoCrete 225 (obtainable from Sika Germany) |

4.2 Rheology Measurements

Tailings can be regarded as so-called Bingham bodies which, unlike Newtonian fluids, begin to flow under the action of force only above a specific shear stress to [Pa] (also called the flow limit). The following relationship applies to the transverse stress τ [Pa]: $\tau=\tau_0+\eta \times \gamma'$. The transverse stress r thus depends on the shear stress $\tau_0$ and the viscosity η [Pa·s] of the Bingham body, as well as on the shear rate γ' [s$^{-1}$].

The rheology measurements on the tailings were carried out using a device of the Schleibinger Viskomat NT type (Schleibinger Geräte, Germany). A rotating measuring paddle (=shear body) is thereby immersed in the sample to be tested. The device measures the torque T, which is transmitted to the measuring paddle in dependence on the speed of rotation and the flow behavior of the sample. The measured torque T can be considered to be proportional to the transverse shear T.

Measurement was carried out analogously to the vane test, which is recognized worldwide in the field of tailings. The test uses a special shear body (measuring paddle) in the form of two rectangular plates which are perpendicular to one another and can be rotated about their longitudinal axes. Specifically, in each case 700 g of the tailings were tested at a shear rate of 1 revolution per minute, and the change in the torque over time was recorded. The maximum torque $T_{max}$ which occurs thereby can be regarded as being proportional to the transverse stress $\tau$.

In each case, a measurement of the pure tailings (without dispersant) was carried out, as well as a corresponding measurement with added dispersants in a predetermined concentration. The relative change in torque ($=T_{max\ (with\ dispersant)}/T_{max\ (without\ dispersant)}$) is considered to be a measure of the activity of the dispersant. When the torque falls, the flowability and/or pumpability of the tailings is improved. An increase results in a corresponding impairment.

4.4 Results

In the following tables, the amount of dispersant added is indicated in the "Dose" column. The value in each case indicates the solids content of the dispersant in question or of the active substance of the dispersant in question, based on the total weight of the tailings.

Table 2 shows the results of the rheology measurements using modified molasses DM, inverted molasses IM and untreated molasses M as dispersants in tailings of the MEL type.

TABLE 2

| Exp. | Dispersant | Dose [% by weight] | Reduction in torque T [%] |
| --- | --- | --- | --- |
| R1 | — | — | 0 |
| A1 | DM | 0.1 | 20.1 |
| A2 | | 0.5 | 44.0 |
| A3 | | 1.0 | 59.4 |
| A4 | | 2.0 | 75.6 |
| B1 | IM | 0.1 | 12.5 |
| B2 | | 0.5 | 32.6 |
| B3 | | 1.0 | 46.4 |
| B4 | | 2.0 | 62.9 |
| C1 | M | 0.1 | 11.0 |
| C2 | | 0.5 | 28.7 |
| C3 | | 1.0 | 42.2 |
| C4 | | 2.0 | 59.1 |

It is apparent from Table 2 that the molasses modified according to the invention DM causes a more pronounced reduction in the measured torque T at all concentrations than does the untreated molasses M or the merely inverted molasses IM. The flowability and/or pumpability of the tailings can thus best be increased by the modified molasses DM.

Table 3 shows a comparison of the dispersing action of modified molasses DM, PAA and PCE in tailings of the DSAL type.

TABLE 3

| Exp. | Dispersant | Dose [% by weight] | Reduction in torque T [%] |
| --- | --- | --- | --- |
| R2 | — | — | 0 |
| D1 | DM | 0.1 | 32.7 |
| D2 | | 0.5 | 68.7 |
| D3 | | 1.0 | 86.8 |

TABLE 3-continued

| Exp. | Dispersant | Dose [% by weight] | Reduction in torque T [%] |
| --- | --- | --- | --- |
| E1 | PAA | 0.1 | 67.0 |
| E2 | | 0.5 | 73.9 |
| E3 | | 1.0 | 74.1 |
| F1 | PCE | 0.1 | −3.1 |
| F2 | | 0.5 | 49.2 |
| F3 | | 1.0 | 96.7 |

It will be noticed that, at low doses (≤0.5% by weight), PAA is the most effective and PCE, surprisingly, is the worst. The activity of DM lies therebetween, but DM is almost equally as effective as PAA at a dose of 0.5% by weight. However, PCE is still far less effective than PAA and DM at 0.5% by weight. At a dose of 1.0% by weight, PCE displays the best action, followed by DM and PAA. Consequently, DM is a particularly advantageous dispersant since it is capable of improving the flowability significantly both at low doses and at higher doses, and is correspondingly easy to meter in.

Table 4 shows a further comparison of the dispersing action of modified molasses DM, PAA and mixtures of DM/PAA, IM/PAA and M/PAA in tailings of the MEL type.

Equal amounts by weight of the two mixture components were used in each of the mixtures. In experiment I1, for example, 0.05% by weight DM and 0.05% by weight PAA was used. The total dose of the dispersants in experiment I1 consequently corresponds to the sum of the two doses and is equal to 0.1% by weight. The same also applies analogously to the other experiments with dispersants in the form of mixtures.

TABLE 4

| Exp. | Dispersant | Dose [% by weight] | Reduction in torque T [%] |
| --- | --- | --- | --- |
| R3 | — | — | 0 |
| G1 | DM | 0.1 | 20.1 |
| G2 | | 0.5 | 44.0 |
| G3 | | 1.0 | 59.4 |
| G4 | | 2.0 | 75.6 |
| H1 | PAA | 0.1 | 44.0 |
| H2 | | 0.5 | 48.1 |
| H3 | | 1.0 | 55.6 |
| H4 | | 2.0 | 63.5 |
| I1 | Mixture of | 0.05 DM/0.05 PAA | 43.7 |
| I2 | DM and PAA | 0.25 DM/0.25 PAA | 53.7 |
| I3 | | 0.5 DM/0.5 PAA | 58.9 |
| I4 | | 1 DM/1 PAA | 84.8 |
| J1 | Mixture of | 0.05 IM/0.05 PAA | 33.3 |
| J2 | IM and PAA | 0.25 IM/0.25 PAA | 56.8 |
| J3 | | 0.5 IM/0.5 PAA | 59.0 |
| J4 | | 1 IM/1 PAA | 75.2 |
| K1 | Mixture of | 0.05 M/0.05 PAA | 34.8 |
| K2 | M and PAA | 0.25 M/0.25 PAA | 56.7 |
| K3 | | 0.5 M/0.5 PAA | 63.1 |
| K4 | | 1 M/1 PAA | 75.1 |

It is apparent from Table 4 that DM and PAA in pure form show similar behavior, as already discussed in connection with Table 3. Of interest, however, in particular the use of mixtures of DM and PAA: At a total dose of 0.1% by weight, the mixture of DM and PAA is capable of reducing the torque almost equally as well as the same amount of PAA alone (compare Experiment I1 with Experiment H1). At total doses of 0.5 and 2.0% by weight, the reductions in torque which can be achieved are even better than with the same amounts of single substances (compare Experiment I2 with Experiment G2 and H2 or Experiment I4 with Experiment G4 and H4). This is surprising since, in mixtures, an average value of the actions of the single components would have been expected. DM and PAA thus act functionally together, that is to say they cause a synergistic effect.

Moreover, a comparison of the mixtures based on DM/PAA with IM/PAA or M/PAA shows that the mixture DM/PAA develops the best action of all the mixtures in particular at the doses in the region of <0.5% by weight which are of particular interest.

The implementation examples shown above serve merely as illustrative examples which can be modified as desired within the scope of the invention. In particular, the above-mentioned cement pastes can additionally contain, for example, aggregates, fillers and/or concrete admixtures. They can especially be mortar or concrete compositions.

Likewise, in the mixtures described in connection with Table 4, for example, compounds according to formula (I) described above can be used instead of or in addition to PAA.

It is also possible to use different mineral suspensions than the described tailings, which, for example, have a lower or a higher solids content. The mineral suspensions can likewise contain coarser-grained particles.

The invention claimed is:

1. A method of using modified molasses as dispersants for a mineral suspension, wherein the modified molasses is obtained according to the following steps:
   a) inverting molasses and/or providing inverted molasses, and
   b) reacting the inverted molasses with alkalis,
   wherein the mineral suspension has a solids content of from 20 to 95% by weight of the total amount of the mineral suspension, and
   wherein the amount by weight of the mineral solid particles in the mineral suspension having a particle size of less than 100 µm is at least 50% by weight of the total amount of all solids in the mineral suspension,
   the method comprising:
      adding the modified molasses to the suspension, and
      dispersing the solid particles in the suspension.

2. The method according to claim 1, wherein the inverting of the molasses in step a) is performed enzymatically with an invertase.

3. The method according to claim 1, wherein the alkaline treatment in step b) is performed with a base selected from the group consisting of Ca(OH)$_2$, Mg(OH)$_2$, NaOH, KOH and mixtures thereof.

4. The method according to claim 1, wherein step b) is carried out at a temperature of from 10° C. to 90° C.

5. The method according to claim 1, wherein in step b), a temperature of from 30° C. to 80° C., and a pH of from 6 to 14, is maintained for 0.5 to 5 hours.

6. The method according to claim 1, wherein the modified molasses is used together with at least one liquefier, and wherein the at least one liquefier has a structure according to formula (I)

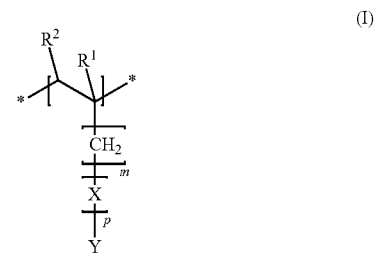

wherein
   $R^1$, independently of one another, represents H or an alkyl group having from 1 to 5 carbon atoms,
   $R^2$, independently of one another, represents H, —COOM, or an alkyl group having from 1 to 5 carbon atoms,
   M, independently of one another, represents an alkali metal ion, an alkaline earth metal ion, a di- or tri-valent metal ion, an ammonium ion, or an organic ammonium group,
   X represents —COO—, —NH— or mixtures thereof,
   m=0, 1 or 2,
   p=0 or 1,
   Y, independently of one another, represents H, M, a $C_1$- to $C_{20}$-alkyl group, -cycloalkyl group, -alkylaryl group, -hydroxyalkyl group, or a group of the formula -[AO]$_n$—$R^a$, wherein the mentioned groups are unsubstituted or substituted by a sulfone group, a sulfate group or by a phosphate group,
   wherein A=$C_2$- to $C_4$-alkylene, $R^a$ represents H, a $C_1$- to $C_{20}$-alkyl group, -cyclohexyl group or -alkylaryl group, and n=1-10.

7. The method according to claim 6, wherein the at least one liquefier includes a poly(meth)acrylic acid and/or a salt thereof.

8. The method according to claim 1, wherein the modified molasses, optionally together with the at least one liquefier, is used in an amount of from 0.01 to 5% by weight, based on the solids content of the mineral suspension.

9. The method according to claim 1, wherein the amount by weight of solid particles having a particle size greater than 10 mm in the mineral suspension is less than 10% by weight, based on the total weight of all the solids in the mineral suspension.

10. The method according to claim 1,
   wherein the modified molasses, optionally together with the at least one liquefier, is used in an amount of from 0.01 to 5% by weight, based on the solids content of the mineral suspension, and
   wherein the amount by weight of solid particles having a particle size greater than 10 mm in the mineral suspension is less than 10% by weight, based on the total weight of all the solids in the mineral suspension.

11. The method according to claim 9, wherein the modified molasses, optionally together with the at least one liquefier, is used in an amount of from 0.01 to 0.8% by weight based on the total weight of the mineral suspension.

12. The method according to claim 1,
   wherein the mineral suspension comprises a mineral binder, and
   wherein the mineral suspension is a mortar composition or a concrete composition.

13. A method for producing a mineral suspension,
wherein modified molasses, as described in claim 1, is mixed with mineral solid particles and a liquid, and
wherein the mineral suspension has a solids content of from 20 to 95% by weight of the total amount of the mineral suspension, and
wherein the amount by weight of the mineral solid particles in the mineral suspension having a particle size of less than 100 μm is at least 50% by weight of the total amount of all solids in the mineral suspension.

14. A mineral suspension obtained by the method according to claim 13.

15. A molded body obtained by hardening a mineral suspension according to claim 14, wherein the mineral suspension comprises mineral binder tempered with water.

16. The method according to claim 1, wherein the amount by weight of solid particles having a particle size of greater than 1 mm is less than 10% by weight of the total amount of all solids.

17. The method according to claim 1, wherein the amount by weight of solid particles having a particle size of greater than 1 mm is less than 1% by weight of the total amount of all solids.

18. The method according to claim 1, wherein the amount by weight of solid particles having a particle size of less than 100 μm is 95% or greater by weight of the total amount of all solids.

19. The method according to claim 1,
wherein step b) is carried out at a temperature of from 30° C. to 80° C. and the temperature is maintained constant for from 1.5 to 4 hours.

20. The method according to claim 1, wherein a total amount of cement, hydraulic binders and mineral binders in the mineral suspension is less than 5% by weight of the total weight of all the solids in the mineral suspension.

21. The method according to claim 1, wherein a total amount of cement, hydraulic binders and mineral binders in the mineral suspension is less than 0.1% by weight of the total weight of all the solids in the mineral suspension.

22. The method according to claim 1, wherein the mineral suspension has a pH of from 5 to 10.

23. The method according to claim 1, wherein the mineral suspension comprises tailings.

24. The method according to claim 1, wherein:
the amount by weight of solid particles having a particle size of greater than 1 mm is less than 10% by weight of the total amount of all solids;
the amount by weight of solid particles having a particle size of less than 100 μm is 95% or greater by weight of the total amount of all solids; and
a total amount of cement, hydraulic binders and mineral binders in the mineral suspension is less than 5% by weight of the total weight of all the solids in the mineral suspension.

* * * * *